US007060714B2

(12) United States Patent
Ahn et al.

(10) Patent No.: US 7,060,714 B2
(45) Date of Patent: Jun. 13, 2006

(54) FUNGAL STRAIN ACREMONIUM SP.MT70646(KCTC 0916BP), NOVEL COMPOUNDS PRODUCED BY THIS STRAIN AND THEIR USE

(75) Inventors: Jong Seog Ahn, Daejeon (KR); Bo Yeon Kim, Daejeon (KR); Won Keun Oh, Daejeon (KR); Tae Ick Mheen, Daejeon (KR); Dae Ook Kang, Daejeon (KR); Hack Ryong Ko, Tongyoung (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 358 days.

(21) Appl. No.: 10/168,807

(22) PCT Filed: Dec. 19, 2000

(86) PCT No.: PCT/KR00/01493

§ 371 (c)(1),
(2), (4) Date: Jun. 21, 2002

(87) PCT Pub. No.: WO01/46385

PCT Pub. Date: Jun. 28, 2001

(65) Prior Publication Data

US 2003/0032603 A1    Feb. 13, 2003

(30) Foreign Application Priority Data

Dec. 21, 1999  (KR)  ............................... 1999/59819

(51) Int. Cl.
*A01N 43/16* (2006.01)
*C12P 19/58* (2006.01)
*C12N 1/14* (2006.01)

(52) U.S. Cl. ..................... 514/332; 435/77; 435/254.1

(58) Field of Classification Search ................ 514/332; 435/77, 254.1, 200
See application file for complete search history.

(56) References Cited

FOREIGN PATENT DOCUMENTS

JP           6247900 A2 * 10/2001

OTHER PUBLICATIONS

Humano et al. (J. Antibiotics (1993) 46(11): 1648-57).*
Ondeyka et al. (J. Antibiotics (2003) 56(12): 1018-1023).*
Ko et al. J. Antibiotics (Feb. 2000) 53(2): 211-214.*
Webster's II New Riverside University Dictionary (Houghton-Mifflin: Boston, MA) (1984), p. 997.*
Kramer, Randall H. et al., Solubilization and Degradation of Subendothelial Matrix Glycoproteins and Proteoglycans by Metastatic Tumor Cells, *The Journal of Biological Chemistry*, 1982, vol. 257, No. 5, pp. 2678-2686.

Di Ferrante, D. et al., Heparan Sulfate Degradation: Relation to Tumor Invasive and Metastatic Properties of Mouse B16 Melanoma Sublines, 1983, *Science*, vol. 220, pp. 611-613.
Vlodavsky, I. et al., Mammalian Heparanase: Gene Cloning, Expression and Function in Tumor Progression and Metastasis, *Nature Medicine*, 1999, vol. 5, No. 7, pp. 793-802.
Hulett, M. et al., Cloning of Mammalian Heparanase, an Important Enzyme in Tumor Invasion and Metastasis, *Nature Medicine*, 1999, vol. 5, No. 7, pp. 803-809.
Irimura, Tatsuro et al., Chemically Modified Heparins as Inhibitors of Heparan Sulfate Specific Endo-glucuronidase (Heparanase) of Metastatic Melanoma Cells, *Biochemistry*, 1986, vol. 25, No. 18, pp. 5322-5328.
Saiki et al., Inhibition by Sulfated Chitin Derivatives of Invasion through Extracellular Matrix and Enzymatic Degradation by Metastatic Melanoma Cells, 1990, *Cancer Research 50*, pp. 3631-3637.
Parish, C. et al., Identification of Sulfated Olgiosaccharide-based Inhibitors of Tumer Growth and Metastasis Using Novel in Vitro Assays for Angiogenesis and Heparanase Activity, 1999, *Cancer Research*, vol. 59, pp. 3433-3441.
Cohen, T. et al., $VEGF_{121}$, a Vascular Endothelial Growth Factor (VEGF) Isoform Lacking Heparin Binding Ability, Requires Cell-surface Heparan Sulfates for Efficient Binding to the VEGF Receptors of Human Melanoma Cells, *The Journal of Biological Chemistry*, 1995, vol. 270, No. 19, pp. 11322-11326.
Soeda, S. et al., Inhibitory Effect of Oversulfated Fucoidan on Tube Formation by Human Vascular Endothelial Cells, *Biol. Pharm. Bull.*, 1997, vol. 20, pp. 1131-1135.
Shiozawa, H. et al., Trachyspic Acid, a New Metabolite Produced by *Talaromyces trachyspermus*, that Inhibits Tumor Cell Haparanese: Taxonomy of the Producing Strain, Fermentation, Isolation, Structural Elucidation, and Biological Activity, *The Journal of Antibiotics*, 1995, vol. 48, No. 5, pp. 357-362.

(Continued)

Primary Examiner—Jean C. Witz
Assistant Examiner—Susan Hanley
(74) Attorney, Agent, or Firm—Jones Day

(57) ABSTRACT

The invention is aimed at discovering a new type of anti-cancer compound which can exert an excellent inhibitory activity against the heparanase. A fungal strain *Acremonium* sp. MT70646 (KCTC 8973P) was isolated from the soil. From the culture of the isolated fungal strain, novel compounds that can inhibit both heparinase and heparanase was purified. Therefore, the present invention regards to provide a newly isolated fungal strain *Acremonium* sp. MT70646 (KCTC 8973P), its new products, and pharmaceutical agents such as a heparinase inhibitor, a heparanase inhibitor, a metastasis inhibitor and an angeiogenesis inhibitor all of which contain the above new compounds produced by the fungal strain as an active ingredient.

7 Claims, 4 Drawing Sheets

OTHER PUBLICATIONS

Kawase, Y. et al., A-72363 A-1, A-2, and C, Novel Heparanase Inhibitors from *Streptomyces nobilis* SANK 60192, II. Biological Activities, *The Journal of Antibiotics*, 1996, vol. 49, No. 1, pp. 61-64.

Nakajima, M. et la., Suramin, a Potent Inhibitor of Melanoma Heparanase and Invasion, *The Journal of Biological Chemistry*, 1991, vol. 266, No. 15, pp. 9661-9666.

* cited by examiner

FUNGAL STRAIN ACREMONIUM SP.MT70646(KCTC 0916BP), NOVEL COMPOUNDS PRODUCED BY THIS STRAIN AND THEIR USE

This application claims priority to Korean application No. 10-1999-59819, filed Dec. 21, 1999, which is incorporated by reference herein in its entirety.

BACKGROUND OF THE INVENTION

1. Field of the Invention

The present invention relates to a fungal strain *Acremonium* sp. MT70646 (KCTC 0916BP) isolated from soil, its novel products and their uses, and more particularly, to an isolated fungal strain *Acremonium* sp. MT70646 (KCTC 0916BP) which produces substances that can inhibit metastasis by inhibiting the activities of heparanase that are needed in angiogenesis or intraepithelial invasion of cancer cells, the novel products isolated and purified from the isolated fungal strain *Acremonium* sp. MT70646 (KCTC 0916BP) expressed as the following formula 1, and the uses of these products as active ingredients of pharmaceutical agents such as a heparinase inhibitor, a heparanase inhibitor, a metastasis inhibitor and an angiogenesis inhibitor.

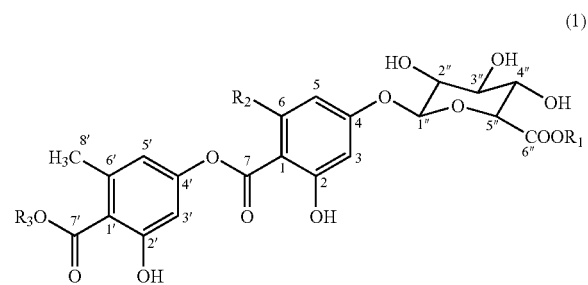

2. Description of the Related Art

Tumor invasion or metastasis progressed in mammalian cells always entails processes of enzymatic decomposition of basement membranes. Heparan sulfate, as in the cases with collagen, laminin and fibronectin are major components present in basement membranes of most mammalian cells. Heparan sulfate and heparin are glycosaminoglycan wherein disaccharides of highly N-acetylated- or N-sulfated glucosamine and hexuronate are continuously linked, and their structures are very similar to each other.

Heparan sulfate and heparin are decomposed by heparanase and heparinase, respectively, and here heparinase is able to decompose heparan sulfate as well as heparin. These enzymes are already known to be closely associated with angiogenesis and metastasis [*J. Biol. Chem.* 257, 2678~2686, (1982); *Science* 220, 313~325, (1983); *Nature Med.* 5, 793~802, (1999); *Nature Med.* 5, 803~809, (1999)]. Moreover, the reports that the inhibitors of these enzymes are also involved in the inhibition of tumors [*Biochemistry.* 25, 5322~5328, (1986); *Cancer Res.* 50, 3631~3637, (1990) *Cancer Res.* 59, 3433~3441, (1999)] have raised the possibilities that these enzyme inhibitors can be used as anti-cancer drugs, and many lines of studies are being conducted still to find other potential anticancer agents.

Metastasis is generally developed by the proliferation of cancer cells mediated by nutrient supply through angiogenesis and for the angiogenesis to occur the presence of vascular endothelial growth factor (VEGF) or basic fibroblast growth factor (bFGF) is essential. These growth factors usually bound to either heparin or heparan sulfate can be separated via decomposition by heparinase or heparanase, which are then able to induce the growth of vascular endothelial cells thus resulting in angiogenesis. Therefore, inhibition of heparanase can result in the inhibition of the angiogenesis thus preventing the growth of cancer cells, especially the growth of metastatic cancer cells [*J. Biol. Chem.* 270, 11322~11326, (1995)]. One of the methods widely used in estimating the level of angiogenesis is to use human umbilical vascular endothelial cells called "HUVEC" [*Biol. Pharm. Bull.* 20, 1131~1135, (1997)]. Examples of known heparanase inhibitors are trachyspic acid [*J. Antibiotics* 48, 357~362, (1994)] and A-72363C [*J. Antibiotics* 49, 61~64, (1996)] and suramin which is clinically used as an anti-cancer drug [*J. Biol. Chem.* 266, 9661~9666, (1991)] is also known to inhibit the activity of heparinase as well as the metastasis of cancer cells. Consequently, it is in urgent need to develop a new therapeutic compound that can inhibit the activities of heparinase and heparanase with a little amount so that it can inhibit the angiogenesis in vivo thus ultimately inhibiting the metastasis.

SUMMARY OF THE INVENTION

The inventors of the present invention had conducted numerous researches to find a new type of anti-cancer compound which can exert an excellent inhibitory activity against the heparanase as a way to solve the above-mentioned problem. The inventors were then able to isolate a fungal strain *Acremonium* sp. MT70646 (KCTC 0916BP) from the soil and succeeded in purification a novel compound expressed by the above formula 1 that can inhibit both heparinase and heparanase from the culture of the isolated fungal strain. Therefore, the object of the present invention is to provide a newly isolated fungal strain *Acremonium* sp. MT70646 (KCTC 0916BP), its new products, and pharmaceutical agents such as a heparinase inhibitor, a heparanase inhibitor, a metastasis inhibitor and an angiogenesis inhibitor all of which contain the above new compounds produced by the fungal strain as an active ingredient.

BRIEF DESCRIPTION OF THE DRAWINGS

FIG. 1 shows the $^1$H-NMR spectrum of the compound CRM646-A represented by formula 1a.

FIG. 2 shows the $^{13}$C-NMR spectrum of the compound CRM646-A represented by formula 1a.

FIG. 3 shows the HBMC spectrum of the compound CRM646-A represented by formula 1a.

DETAILED DESCRIPTION OF THE INVENTION

Figure 1:
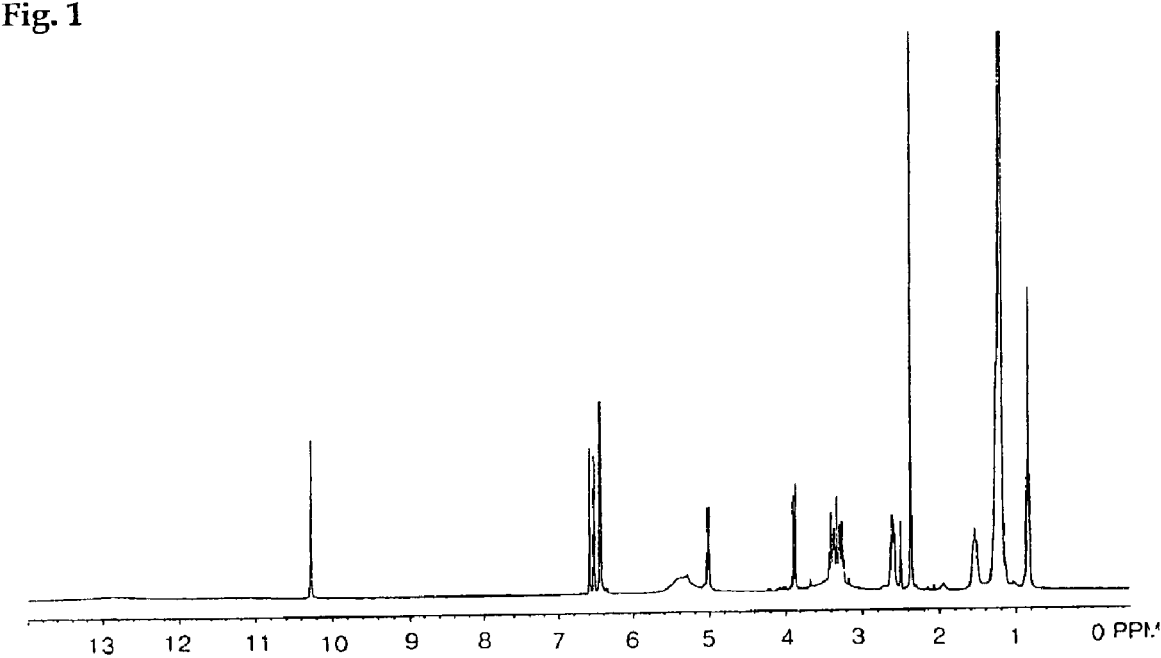

This invention relates to a newly isolated fungal strain *Acremonium* sp. MT70646(KCTC 0916BP). This invention also relates to a compound expressed by the following formula 1 which is useful as an anti-cancer agent by having inhibitory activities against a heparinase, a heparanase, metastasis and aniogenesis,

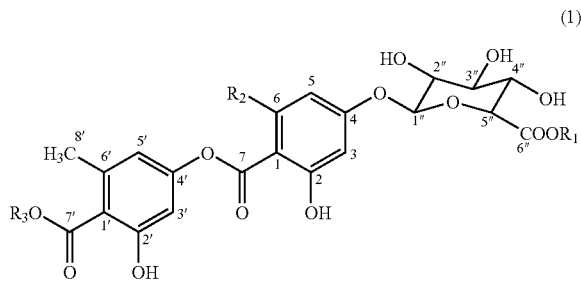

(1)

wherein $R_1$ represents a hydrogen atom, a halogen atom, or a $C_1$–$C_6$ alkyl group; $R_2$ represents a $C_1$–$C_{20}$ alkyl group; and $R_3$ represents a hydrogen atom, a halogen atom, or a $C_1$–$C_6$ alkyl group.

This invention is explained in more detail as set forth hereunder.

The isolation and identification of the fungal strain *Acremonium* sp. MT70646 (KCTC 0916BP) according to the present invention are as follows.

(1) Isolation of a Fungal Strain

To 10 mL of sterilized physiological saline was added 1 g of air-dried soil, mixed for 30 min and diluted $10^{-2}$~$10^{-4}$. 0.1 mL of the diluted mixture was then smeared on potato dextrose agar medium, cultured at 25° C. for 7–10 days and colonies were isolated.

(2) Identification of the Isolated Fungal Strain

1) Morphological and Cultural Characteristics

The above newly isolated fungal strain MT70646 possesses the typical morphology of fugal stain and its cultural characteristics are as follows. First, the color of fungal colonies cultured in potato dextrose agar was whitish at the beginning of growth and turned to light orange in the center of colonies, and after 14 days the round colony of culture became approximately 3.5 cm in diameter. After 14 days, the area of medium where fungal hyphae grew became hard and there were formed whitish aerial hyphae from the old colonies with light orange color located in the center of the medium. Microscopic observations revealed that there were lengthy extensions of hyphae like a thread each of which having a thickness of 2.0–2.5 μm and they were intermingled with each other to form clusters consisting of tens of hyphae. The big clusters were interconnected like a net while each hypha was branching out into multi-directions in small clusters. The color of fungal culture also changed from the initial light yellow to brown at the end of the culture.

2) Physiological Characteristics

The growth of MT70646 in liquid medium reached its maximum on the sixth day of culture and the new product produced by the fungal strain reached its maximum level on day 5. The optimum temperature of culture for the production was 26° C. The pH of culture started at pH 6.8, dropped to pH 5.5 three days after the culture and gradually rose again to pH 7.5–8.0 by the time of completion. The culture was grown under 1.0 vvm of aeration and 300 rpm of agitation at 26° C.

3) Identification of Fungal Isolate MT70646 and Nomenclature

The morphological, cultural and physiological characteristics of the isolated fungal strain MT70646 are summarized in the following Table 1, and the isolated strain MT70646 was confirmed to be an *Acremonium* sp. from *Medically Important fungi* [*Medically Important Fungi*, 1995, ASM press, Washington D.C.] and *Compendium of soil fungi* [*Compendium of Soil Fungi*, 1980, Academic Press, London]. Hence, the isolated fungal strain in the present invention was named *Acremonium* sp. MT70646 and cordially deposited to the Korean Collection for Type Cultures (KCTC) in Korea Research Institute of Bioscience and Biotechnology (KRIBB) on Nov. 5, 1999 to receive depository number KCTC 8973P. On Dec. 15, 2000, this deposit was converted to a deposit under the Budapest Treaty, and the strain was re-designated KCTC 0916BP.

TABLE 1

| Morphological and Cultural Characteristics | |
| --- | --- |
| Colony | Slow Growth Rate |
| | Diameter of colony is 3.5 cm after 14 days of culture in PDA medium |
| | The initial color is white but changes into light orange from the central area as it grows. |
| | Color of back is light orange. |
| Hyphae | Transparent |
| | 2.0–2.5 μm in diameter |
| | Forms drill-shaped upright phialide |
| Conidium | Forming clusters |
| | Clusters branched out from the end of phialide |
| | Cylindrical or spherical form with a size of 4.0–8.0 μm in diameter |

(3) Culture of the Isolated Fungal Strain

The isolated fungal strain MT70646 is cultured in the medium containing nutrients used for fungal culture. For example, glucose, fructose, etc. are used as a carbon source and peptone and trypton, etc. are used as a nitrogen source. Other nutrient sources such as magnesium sulfate and inorganic salts can be added as needed and submerged culture method under aerobic condition at 23–28° C. is recommended to culture the fungal strain.

As seed culture medium and production medium is used a medium containing 0.3% yeast extract, 0.3% malt extract, 0.5% peptone, 2% glucose, 0.05% magnesium sulfate: $7H_2O$, 0.1% potassium dihydrogen phosphate. Two hundred milliliter of seed culture medium in a 1 L Erlenmyer flask was sterilized by autoclaving for 20 mm at 121° C. and inoculated with slant cultured MT70646 (KCTC 0916BP) and cultured for 5 days at 26° C. under aerobic conditions (aeration with 1.0 vvm) while providing agitation of 300 rpm.

(4) Isolation and Purification of the Inhibitors Produced by the Fungal Train MT70646 (KCTC 0916BP)

*Acremonium* sp. MT70646 culture was extracted using butanol, concentrated via vacuum evaporation using a vacuum dryer, and purified the compounds as expressed in the above formula 1.

The formula 1 is abbreviated in the present invention as follows.

When $R_1$ is H, $R_2$ is $(CH_2)_{14}CH_3$, and $R_3$ is H, the compound of formula 1 becomes 6-[(4-carboxy-3-hydroxy- 5-methyl-phenoxycarbonyl)-3-hydroxy-5-pentadecyl-phenoxyl]-3,4,5-trihydroxy-tetrahydro-pyran-2-carboxylic acid as expressed in the following formula 1a and is abbreviated as "CRM646-A".

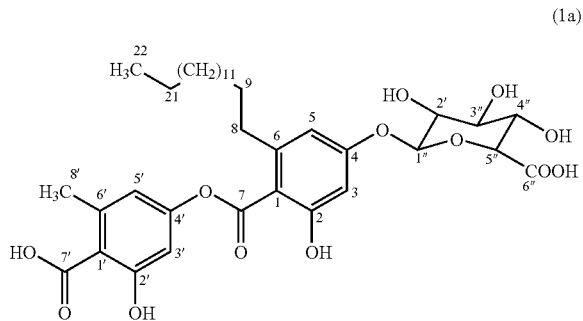

(1a)

When $R_1$ is $CH_3$, $R_2$ is $(CH_2)_{14}CH_3$, and $R_3$ is H, the compound of formula 1 becomes 6-[(4-carboxy-3-hydroxy-5-methyl-phenoxycarbonyl)-3-hydroxy-5-pentadecyl-phenoxyl]-3,4,5-trihydroxy-tetrahydro-pyran-2-carboxylic methyl ester as expressed in the following formula 1b and is abbreviated as "CRM646-B".

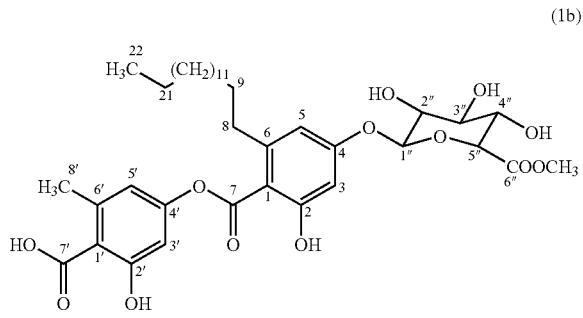

(1b)

The structural analyses of the above compounds related to the formula 1 can be summarized as follows.

Figure 2:
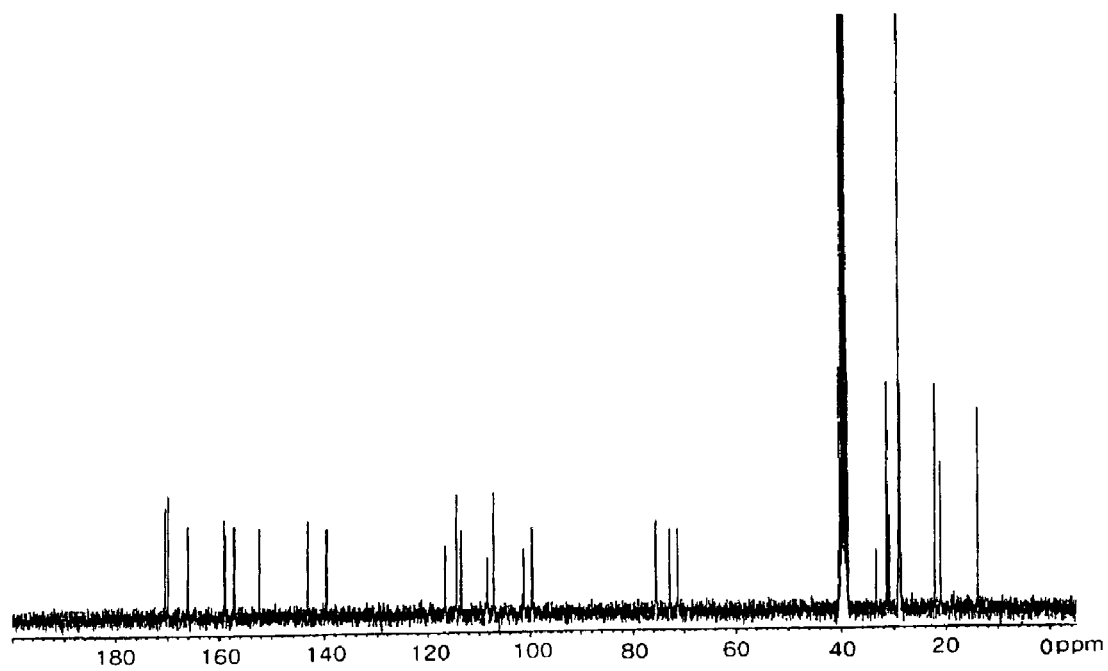
Figure 3:
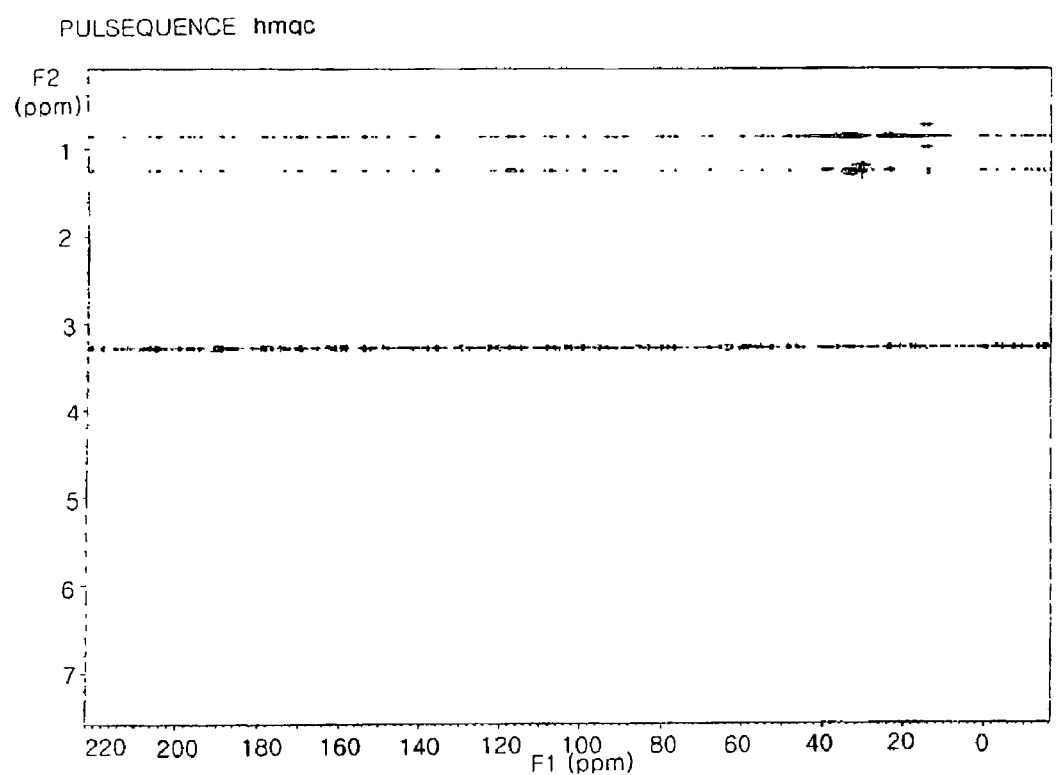

The compound CRM646-A expressed as formula 1a was white powder which was well dissolved in solvents such as ethanol, butanol, dimethyl sulfoxide(DMSO), however, it was not dissolved easily in water, hexane and chloroform. UV absorption spectrum analyses revealed that the maximum absorption was shown at wavelengths of 214 nm, 260 nm and 305 nm, and the result of high resolution FAB (fast atom bombardment) mass spectrometry (HRFAB-MS) showed that the molecular weight of the CRM646-A is 690 and its molecular formula is $C_{36}H_{50}O_{13}$. The results of infrared (IR) absorption spectrum; $^1$H-NMR and $^{13}$C-NMR spectrum; and HMBC NMR spectrum analyses are shown in the Tables 2 & 3 and FIGS. 1–3.

The results confirmed that the compound CRM646-A is a novel compound having a structure as shown in the above formula 1a. The structure of CRM646-A appears very similar to TPI-3 and TPI-4, which are known to have inhibitory activities against cAMP phosphodiesterase, in that they have the same molecular weight and also very similar structures (Jpn Kokai 215551('87), Sep. 22, 1987), however, the differences in the length, location, and the kinds of sugar (glucuronic acid) of aliphatic carbon linked to another ring distinguishes the present compound CRM646-A from them, thus confirming that CRM646-A is a new biologically active substance that possesses inhibitory activities against heparinase and heparanase.

Figure 4:
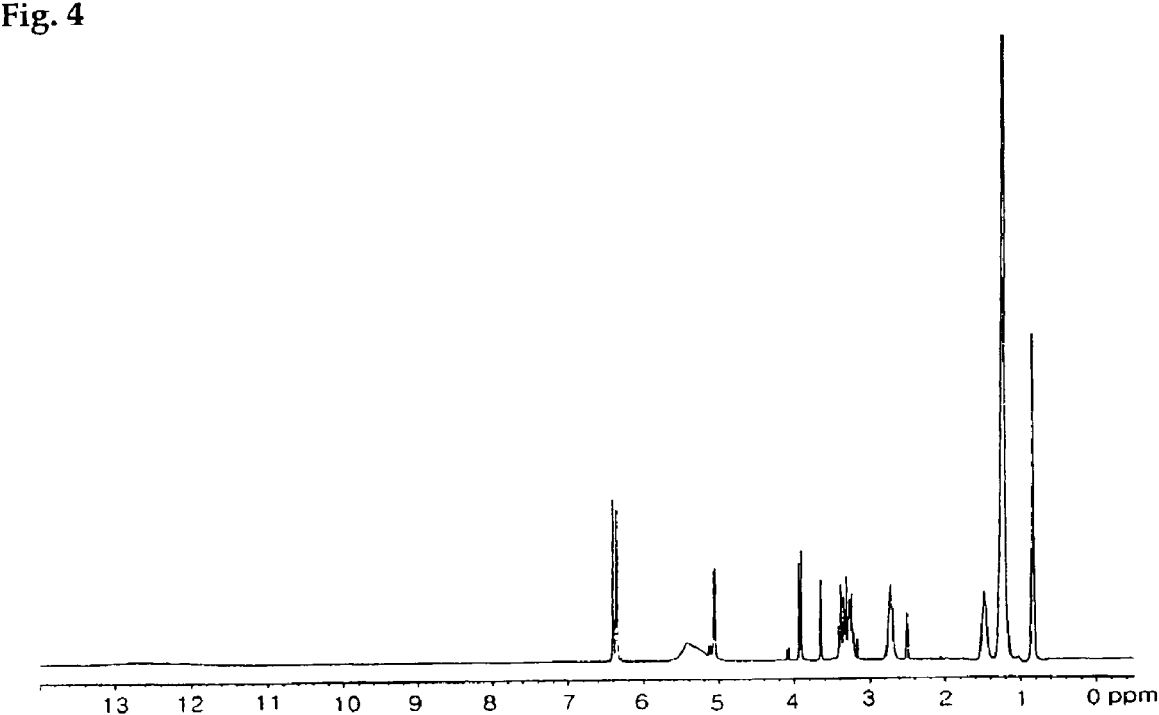
FIG. 4 shows the $^1$H-NMR spectrum of the compound CRM646-B represented by formula 1b.
Figure 5:
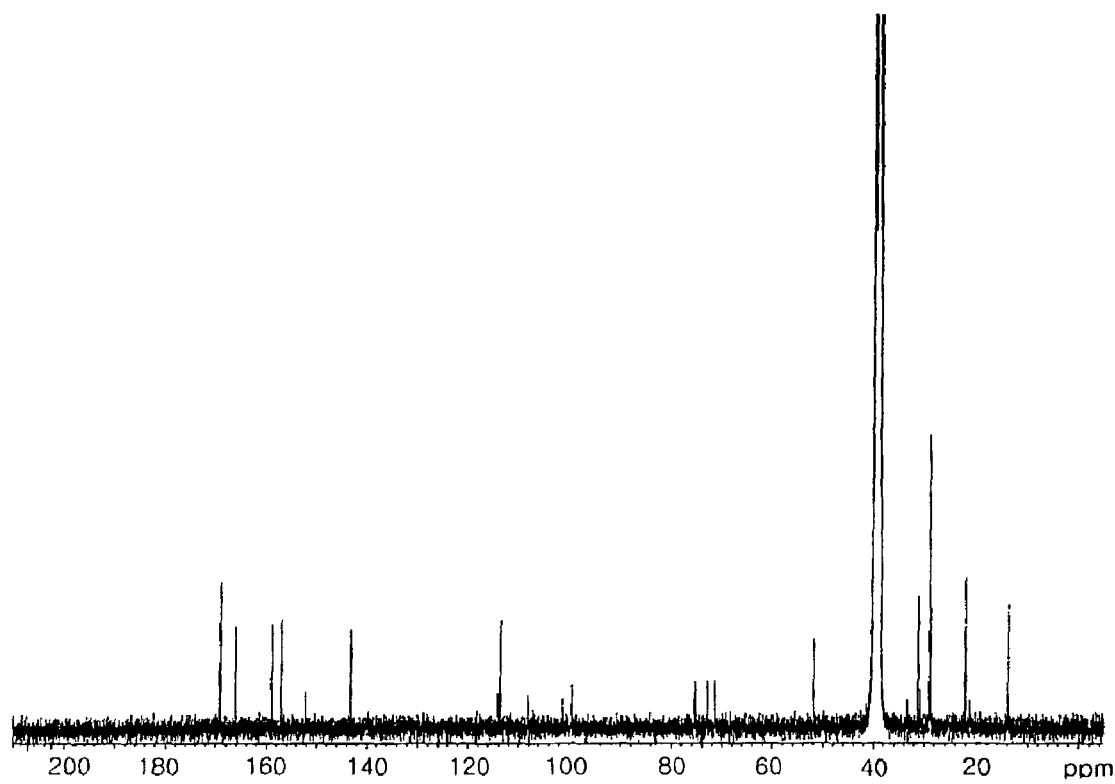
FIG. 5 shows the $^{13}$C-NMR spectrum of the compound CRM646-B represented by formula 1b.

Likewise, the compound CRM646-B expressed as formula 1b is a derivative of the CRM646-A and the HRFAB-MS result revealed that its molecular weight is 704 and its molecular formula is $C_{37}H_{52}O_{13}$. The physicochemical properties of the compound CRM646-B was almost same as in the compound CRM646-A. The results of IR absorption spectrum analysis is shown in the following Table 2 while the analyses of $^1$H-NMR and $^{13}$C-NMR spectrum are shown in the following Table 3 and the analyses of $^1$H NMR and $^{13}$C-NMR spectrum are shown in the following FIGS. 4 and 5, respectively. According to the results, there was a new peak at 3.66 ppm in $^1$H-NMR spectrum and a new peak at 51.95 ppm in $^{13}$C-NMR spectrum thus implying the presence of methoxy ($OCH_3$) group. This reveals that CRM646-B was sustituted with methoxy group at the carboxyl group of C-6 of glucuronic acid which is present in the compound CRM646-A. Therefore, the compound CRM646-B, being as a modified derivative of the compound CRM646-A, is also a new biologically active substance as is the case with the compound CRM646-A.

TABLE 2

| Physico-Chemical Properties | | |
|---|---|---|
| Compounds | CRM646-A (1) | CRM646-B (2) |
| Color & Shape | White Powder | White Powder |
| Molecular Formula | $C_{36}H_{50}O_{13}$ | $C_{37}H_{52}O_{13}$ |
| HRFAB-MS | | |
| Calculated Data | 691.7965 | 705.8235 |
| Experimental Data | 691.7931 | 705.8265 |
| Melting Point (° C.) | 143–144 | 145–146 |
| UV Absorption Spectrum ($\lambda_{max}$ in MeOH) | 214, 260, 305 | 214, 262, 306 |
| IR Absorption Spectrum (cm$^{-1}$, KBr) | 3397, 2924, 1730, 1666, 1420, 1314, 1244, 1178 | 3395, 2925, 1731, 1667, 1614, 1423, 1315, 1250 |

TABLE 3

| $^1$H- and $^{13}$C-NMR Spectrum Analyses of CRM646-A and CRM646-B | | | | |
|---|---|---|---|---|
| | CRM646-A | | CRM646-B | |
| No. | $^1$H | $^{13}$C | $^1$H | $^{13}$C |
| 1 | | 113.53 | | 113.63 |
| 2 | | 157.16 | | 157.13 |
| 3 | 6.45(br.s) | 101.27 | 6.45(br.s) | 101.34 |
| 4 | | 159.12 | | 159.23 |
| 5 | 6.45(br.s) | 108.31 | 6.45(br.s) | 108.26 |
| 6 | | 143.18 | | 143.17 |
| 7 | | 166.15 | | 166.15 |
| 8 | 2.60(m) | 33.41 | 2.60(m) | 33.39 |
| 9 | 1.54(m) | 30.84 | 1.54(m) | 30.79 |
| 10 | 1.26(m) | 28.70 | 1.26(m) | 28.68 |
| 11 | 1.18–1.26(m) | 28.81 | 1.18–1.26(m) | 28.80 |
| 12 | 1.18–1.26(m) | 28.88 | 1.18–1.26(m) | 28.90 |
| 13–18 | 1.18–1.26(m) | 29.03(×6) | 1.18–1.26(m) | 29.01(×6) |
| 19 | 1.18–1.26(m) | 28.94 | 1.18–1.26(m) | 28.91 |
| 20 | 1.18–1.26(m) | 31.29 | 1.18–1.26(m | 31.27 |
| 21 | 1.22(m) | 22.09 | 1.21(m) | 22.08 |
| 22 | 084(t, 6.5) | 13.95 | 084(t, 6.0) | 13.95 |
| 1' | | 116.74 | | 116.53 |
| 2' | | 158.77 | | 158.99 |
| 3' | 6.58(d, 2.0) | 107.15 | 6.56(d, 2.0) | 107.15 |
| 4' | | 152.32 | | 152.26 |

TABLE 3-continued $^1$H- and $^{13}$C-NMR Spectrum Analyses of CRM646-A and CRM646-B

| | CRM646-A | | CRM646-B | |
|---|---|---|---|---|
| No. | $^1$H | $^{13}$C | $^1$H | $^{13}$C |
| 5' | 6.53(d, 1.5) | 114.42 | 6.51(d, 1.5) | 114.26 |
| 6' | | 139.49 | | 139.68 |
| 7' | | 170.55 | | 170.45 |
| 8' | 2.37(s) | 20.99 | 2.37(s) | 21.12 |
| 1" | 5.02(d, 8.0) | 99.67 | 5.08(d, 8.0) | 99.56 |
| 2" | 3.25(dd, 9.0, 7.0) | 72.90 | 3.35(dd, 9.5, 7.5) | 72.85 |
| 3" | 3.32(dd, 9.0, 8.5) | 75.71 | 3.41(dd, 9.0, 8.5) | 75.47 |
| 4" | 3.39(dd, 9.5, 9.5) | 71.35 | 3.52(dd, 9.5, 9.5) | 71.39 |
| 5" | 3.87(d, 9.5) | 75.53 | 4.03(d, 9.5) | 75.23 |
| 6" | | 170.03 | | 169.14 |
| 7" | | | 3.66(s) | 51.95 |
| 2-OH | 10.27(s) | | 10.28(s) | |

The present invention includes a heparinase inhibitor, a heparanase inhibitor, a metatasis inhibitor and an angiogenesis inhibitor which contains the compound expressed in the formula 1 as an active ingredient. The inventors is invention for the first time identified the inhibitory activities of the compounds expressed as the formula 1 purified from the isolated fungal strain *Acremonium* in sp. MT70646 (KCTC 8973P) against the heparinase and heparanase, and accordingly developed anti-cancer pharmaceutical drugs containing the above-mentioned compounds as an active ingredient.

The pharmaceutical composition according to the present invention can be prepared in the form of Tablets, powder, granules, capsules, suspensions, emulsifying liquids for oral supplement and parenteral unit medications or multiple medications by using carriers or excipients known to the artisans pertinent to this art in addition to the active ingredients expressed in the above formula 1. The amount of the effective medication of an active ingredient expressed in the above formula 1 can vary depending on the age and physical conditions such as body weight, and it usually ranges 1–100 mg/kg(body weight)/day and the daily medication can be administered from one to a few times within the permitted daily dosage.

This invention is explained in more detail based on the following examples but they should not be construed as limiting the scope of this invention.

EXAMPLE 1

Culturing *Acremonium* sp. MT70646 (KCTC 0916BP)

As seed culture medium and production medium for *Acremonium* sp. MT70646 (KCTC 0916BP) is used a medium containing 0.3% yeast extract, 0.3% malt extract 0.5% peptone 2% glucose, 0.05% magnesium sulfate 7H$_2$O, 0.1% potassium dihydrogen phosphate. Two hundred milliliter of seed culture medium in a 1 L Erlenmeyer flask was sterilized by autoclaving for 20 mm at 121° C., inoculated with MT70646 slant cultured in PD (potato dextrose) agar or YM (yeast extract and malt extract) Agar medium using a platinum loop and grew in a shake culture for 4 days at 26° C. to produce a seed culture for a fermentor. Ten liters of production medium was added into a 15 L jar fermentor and sterilized by autoclaving for 1 hr at 121° C. inoculated with 200 mL of the above seed culture of MT70646 (KCTC 0916BP) and grew for 5 days at 26° C. under aerobic condition of 1.0 vvm aeration while providing agitation of 300 rpm.

EXAMPLE 2

Isolation and Purification of CRM646-A and CRM646-B

Figure 6:
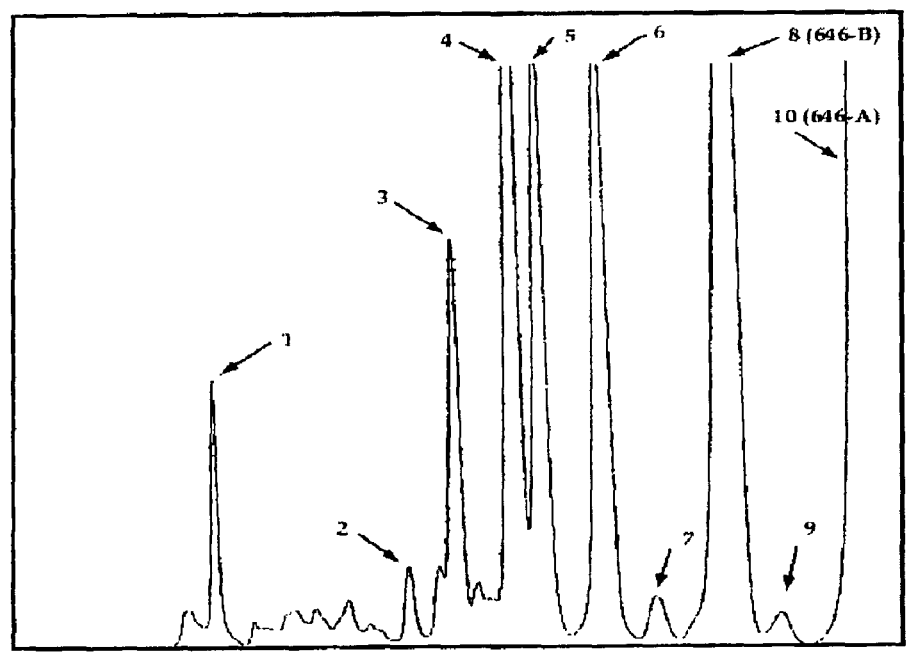
FIG. 6 shows the HPLC elution profile of the compounds produced by the isolated fungal strain *Acremonium* sp. MT70646 (KCTC 0916BP). The numbered peaks indicate the different derivatives separated by HPLC; i.e., the peak 8 is CRM646-B and peak 10 is CRM646-A.

The *Acremonium* sp. MT70646 (KCTC 0916BP) culture was extracted for 3 hrs by adding equal amount of acetone, concentrated under vacuum condensation, resuspended in adequate amount of water, and extracted 3 times using equal amount of butanol to obtain crude extract. This crude extract was adsorbed to silica gel and performed silica gel column chromatography. The active fractions were eluted out stepwise by increasing the concentration of methanol using a mixed solvent of chloroform/methanol (20/1: v/v). The eluted active fractions were concentrated under vacuum condensation and RP-18 column chromatography was performed using 60% acetonitrile as an eluting solvent. The active fractions were reconcentrated, dissolved in small amount of 50% acetonitrile and performed Sephadex LH-20 column chromatography using 60% acetonitrile as an eluting solvent. The active fractions were concentrated to obtain light yellow powder and then separate to pure compounds under high performance liquid chromatography (HPLC) (column: J' sphere ODS-H80, solvent: 80% acetonitrile containing 0.05% trifluoroacetic acid, flow rate: 5 mL/min, detection: 210 nm). More than 10 compounds could be isolated by this HPLC procedure, and FIG. 6 shows the HPLC elution profile of these compounds produced by the isolated fungal strain *Acremonium* sp. MT70646 (KCTC 0916BP). The numbered peaks indicate the different derivatives separated by HPLC. CRM646-A was eluted with the retention time of 17 min and CRM646-B with the retention time of 26 min, which were then concentrated under vacuum condensation to obtain white powder.

EXAMPLE 3

Analysis of the Inhibitory Activities of CRM646-A and CRM646-B Against Heparinase To 17 μL of reaction buffer (14 mM sodium acetate and 1.4 mM CaCl$_2$, pH 7.0) containing 10 ng of heparin were added 3 μL of test sample along with 0.2 unit of heparinase and placed at room temperature for 15 min. Then, 25 μL of antithrombin III solution was added and allowed to react for 2 min at room temperature and added with 25 μL of factor Xa solution. In one minute, 25 μL of factor Xa substrate was added to react for 5–10 min and then terminated the reaction by adding 25 μL of glacial acetic acid. The light absorbency was measured at 410 nm. The rate of enzyme inhibition was calculated as in the following equation 1, wherein IC$_{50}$ was the concentration of the inhibitor when the rate of enzyme inhibition reached 50%.

$$\text{Inhibition (\%)} = (A-C)/(A-B) \times 100 \quad \text{[Equation 1]}$$

In the above equation 1, A represents the light absorbance of the reagent after reaction when the inhibitor was not added, B represents the light absorbance of the reagent after reaction when enzyme solution was not added, and C represents the light absorbance of the reagent after reaction when the inhibitor was added.

The IC$_{50}$ of the newly isolated compounds CRM646-A and CRM646-B when they inhibit the activity of heparinase by 50%, was measured and they were 3 μM and 25 μM, respectively. The heparinase used in this experiment was purchased from Sigma Co. Ltd. (U.S.A.), wherein the heparinase was isolated from *Flavobacterium heparinum*.

EXAMPLE 4

Analysis of the Inhibitory Activities of CRM646-A and CRM646-B Against Heparanase To 17 μL of 0.05M sodium acetate buffer solution (pH 5.1) containing 0.1 mg of bovine serum albumin (BSA) and 5 mM N-acetylmannosemine were added 3 μL of test sample along with 90 pmol of heparan sulfate radio-labeled by $^3$H and 10 ng of heparanase derived from human platelets and allowed to react for 30 min at 37° C. After the reaction, the reaction mixture was passed through a column filled with HRG-Sepharose beads and eluted out the degraded heparan sulfate by heparanase to measure the radioactivity. The rate of enzyme inhibition was calculated as in the following equation 2, wherein $IC_{50}$ was the concentration of the inhibitor when the rate of enzyme inhibition reached 50%.

$$\text{Inhibition (\%)} = (A-C)/(A-B) \times 100 \quad \text{[Equation 2]}$$

In the above equation 2, A represents the radioactivity of the reaction when the inhibitor was not added, B represents the radioactivity of the reaction when enzyme solution was not added, and C represents the radioactivity of the reaction when the inhibitor was added.

The $IC_{50}$ of the newly isolated compounds CRM646-A and CRM646-B when they inhibit the activity of heparanase by 50%, was measured and both of them were 10 μM.

EXAMPLE 5

Inhibitory Activities of CRM646-A and CRM646-B Against the Invasion of B16 Melanoma Cells (Matrigel Invasion)

BioCoat invasion chamber (precoated Matrigel) was swelled for 30 min by serum-free DMEM and the chamber was placed into the well of 24 well plate which contains 600 μL of HT 1080 conditioned medium. And then 450 μL of melanoma cell suspension (4.5×10$^3$ cells) in DMEM medium containing 0.5% albumin was added into the chamber. After adding 50 μL of test sample, the chamber was incubated for 22–24 hr at 37° C. in a 5% CO2 atmosphere. And the filter of chamber was detached and fixed with methanol. After staining the filter with 5% crystal violet and the cells on the upper surface of the filters were removed by wiping them with a cotton swab. The cells invaded through the Matrigel and filter to the lower surface were counted under a microscope.

TABLE 4

Inhibitory Activities of CRM646-A and CRM646-B against the Invasion of B16 Melanoma Cells

| Compounds Tested | Conc. of Reagent (μg/mL) | No. of Cells Invaded | Relative Rate of Invasion (%) |
|---|---|---|---|
| Control | 0 | 420.7 ± 15.6 | 100 |
| CRM646-A | 1 | 421.0 ± 15.6 | 100.1 |
|  | 3 | 384.4 ± 9.4 | 91.4 |
|  | 10 | 300.8 ± 10.2 | 71.5 |
| CRM646-B | 1 | 376.7 ± 19.7 | 89.5 |
|  | 3 | 155.3 ± 18.6 | 36.9 |
|  | 10 | 56.0 ± 8.9 | 13.3 |

As shown above, CRM646-A showed relatively lower activity, however CRM646-B is estimated to have the $IC_{50}$ value of about 2 μg/mL and it showed above 80% inhibitory activity at 10 μg/mL.

Figure 7:
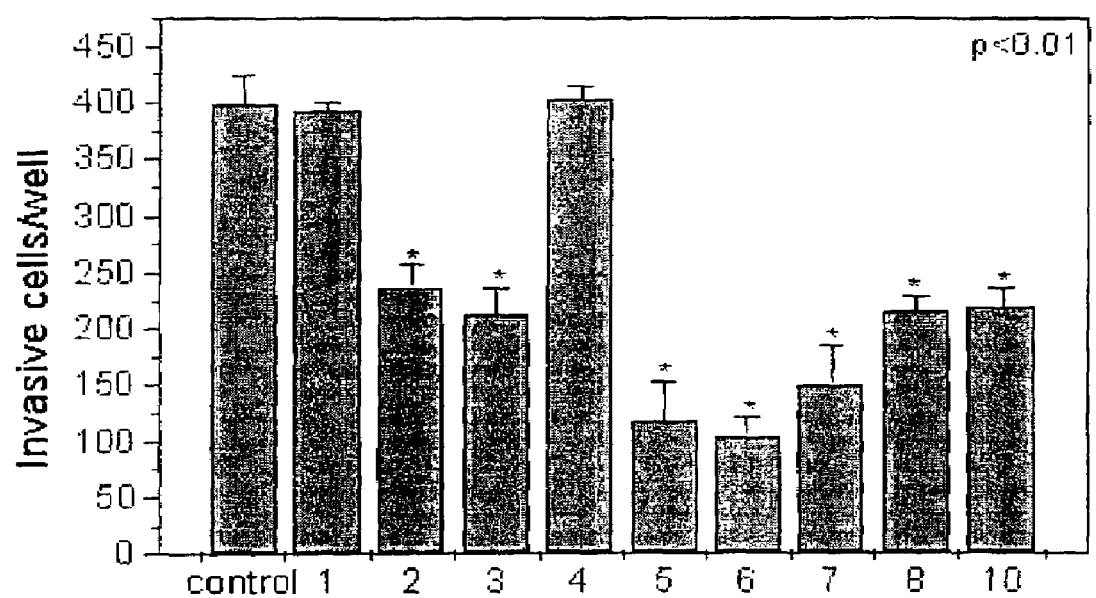
FIG. 7 shows the inhibitory activities of the derivatives (in FIG. 6) produced by the isolated fungal strain *Acremonium* sp. MT70646 (KCTC 0916BP) against the invasion of B16 melanoma cells through the synthetic basal membranes. The bars represent the invaded cell numbers of B16 melanoma treated with each compound at the concentration of 10 μg/mL.

And the other compounds (as shown in FIG. 6) produced by *Acremonium* sp. MT70646 (KCTC 0916BP) have the inhibitory activity against the invasion of B16 melanoma cells through matrigel. Compound 5 and 6 show more potent inhibitory activity than CRM646-B as shown in FIG. 7. In FIG. 7, the bars represent the invaded cell numbers of B16 melanoma treated with each compound at the concentration of 10 μg/mL.

EXAMPLE 6

Inhibitory Activity of CRM646-A and CRM646-B Against Angiogenesis

After thawing Matrigel on ice, 40 μL of the Matrigel was added into each wells of a 96 well plate and placed for 30 min at 37° C. to solidify the Matrigel. Then, 180 μL of human umbilical vein enothelial cell (HUVEC) suspension (2×10$^4$ cells) was added made into each well of the solidified Matrigel and incubated for 18 hr in a 5% CO$_2$ atmosphere at 37° C. The degree of tube formation was observed by microscope.

TABLE 5

Inhibitory Activities of CRM646-A and CRM646-B against the Angiogenesis

| Conc. of Reagent | Compounds Tested | |
|---|---|---|
| (μg/mL) | CRM646-A | CRM646-B |
| 1 | — | — |
| 3 | — | 30% |
| 10 | 30% | 60% |

As shown above, CRM646-B showed a higher inhibitory activity against the angiogenesis than CRM646-A and the inhibitory activity was 60% at the concentration of 10 μg/mL.

EXAMPLE 7

Toxicity Test

In order to examine the toxicity of the new compounds expressed by the formula 1, 10 mice were intraperitoneally administered with 300 mg/kg of the compounds for 14 days and the behavioral abnormalities as well as their survival were observed. There were no abnormal behaviors in the above-medicate mice and all of them survived over until the last day of the experiment. Moreover, there were no significant differences between the medicated mice and those not medicated from the statistical point of view. Therefore, it is speculated that the new compounds have no toxicity under the 300 mg/kg.

EXAMPLE 8

Preparation of Tablets

| Active Ingredient | 10 g |
|---|---|
| Lactose | 70 g |
| Crystalline Cellulose | 15 g |
| Magnesium Stearate | 5 g |
| Total | 100 g |

The above ingredients were crushed into minute particles and then mixed to prepare tablets by using a direct tableting method. The total amount of each tablet was 100 mg and the active ingredient was accounted for 10 mg.

EXAMPLE 9

Preparation of Powdered Agent

| Active Ingredient | 10 g |
|---|---|
| Corn Starch | 50 g |
| Carboxy Cellulose | 40 g |
| Total | 100 g |

The above ingredients were crushed and mixed into powder. 100 mg of powder was added into each hard capsule preparation.

EXAMPLE 10

Preparation of Injection

| Active Ingredient | 1 g |
|---|---|
| Sodium Chloride | 0.6 g |
| Ascorbic Acid | 0.1 g |
| Sterile Water for injection | Adequate |
| Total | 100 g |

100 mL of injection solution was prepared as shown in the above. This solution containing 10 mg of active ingredient was added into an injection ampoule and was sterilized by heating for 30 min at 20° C.

As shown above, the new compounds expressed as the formula 1 produced by *Acremonium* sp. MT70646 (KCTC 0916BP) in the present invention were shown to have excellent inhibitory activities against heparinase and heparanase. Therefore, compositions that contain the above new compounds as an active ingredient are very effective in inhibiting the activities of a heparinase, a heparanase, metastasis and angiogenesis.

What is claimed is:

1. A compound having the following structure (1),

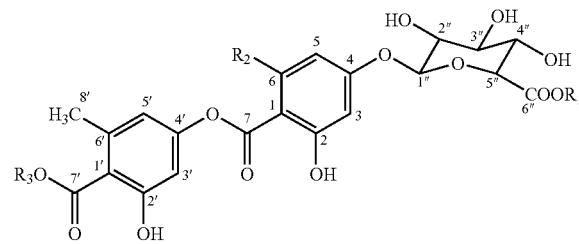

(1)

wherein $R_1$ is a hydrogen atom, a halogen atom, or a $C_1$–$C_6$ alkyl group; $R_2$ is a $C_1$–$C_{20}$ alkyl group; and $R_3$ is a hydrogen atom, a halogen atom, or a $C_1$–$C_6$ alkyl group.

2. A compound according to claim 1 having the following structure (1a).

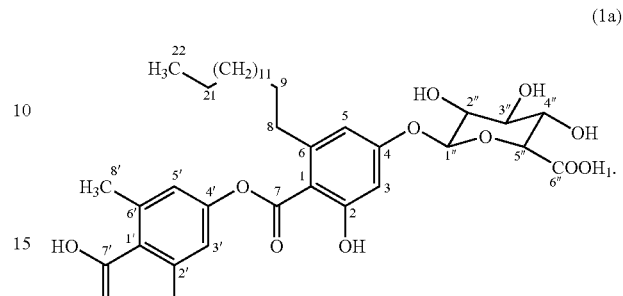

(1a)

3. A compound according to claim 1 having the following structure (1b).

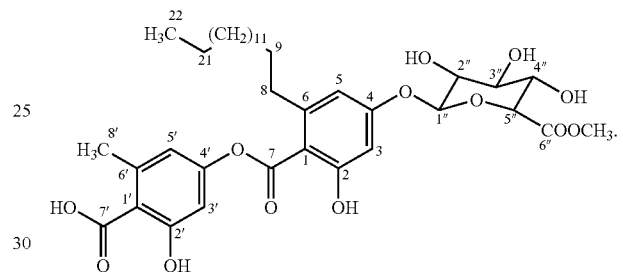

4. A heparinase inhibitor comprising a compound having the following structure (1) as an active ingredient,

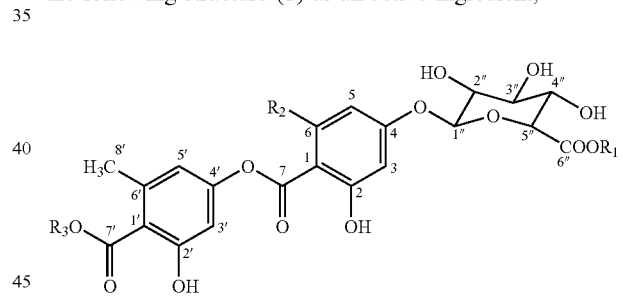

wherein $R_1$ is a hydrogen atom, a halogen atom, or a $C_1$–$C_6$ alkyl group; $R_2$ is a $C_1$–$C_{20}$ alkyl group; and $R_3$ is a hydrogen atom, a halogen atom, or a $C_1$–$C_6$ alkyl group.

5. A heparanase inhibitor comprising a compound having the following structure (1) as an active ingredient,

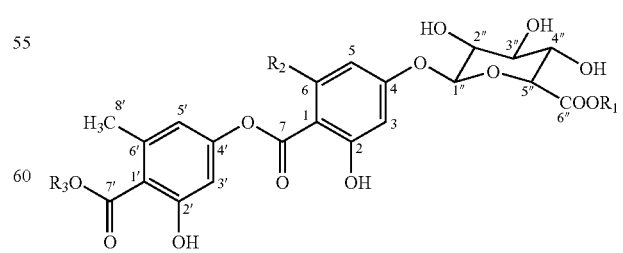

wherein $R_1$ is a hydrogen atom, a halogen atom, or a $C_1$–$C_6$ alkyl group; $R_2$ is a $C_1$–$C_{20}$ alkyl group; and $R_3$ is a hydrogen atom, a halogen atom, or a $C_1$–$C_6$ alkyl group.

6. A metastasis inhibitor comprising a compound having the following structure (1) as an active ingredient,

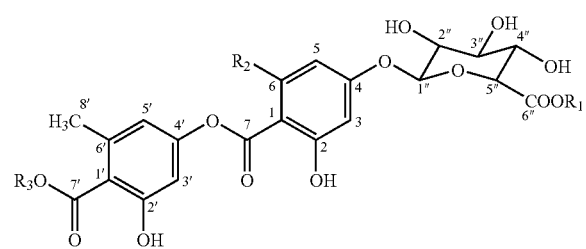

wherein $R_1$ is a hydrogen atom, a halogen atom, or a $C_1$–$C_6$ alkyl group; $R_2$ is a $C_1$–$C_{20}$ alkyl group; and $R_3$ is a hydrogen atom, a halogen atom, or a $C_1$–$C_6$ alkyl group.

7. An angiogenesis inhibitor comprising a compound having the following structure (1) as an active ingredient

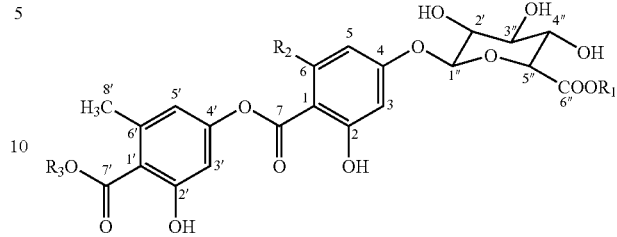

wherein $R_1$ is a hydrogen atom, a halogen atom, or a $C_1$–$C_6$ alkyl group; $R_2$ is a $C_1$–$C_{20}$ alkyl group; and $R_3$ is a hydrogen atom, a halogen atom, or a $C_1$–$C_6$ alkyl group.

* * * * *